(12) United States Patent  
Egilsson

(10) Patent No.: US 7,632,315 B2
(45) Date of Patent: Dec. 15, 2009

(54) VACUUM CHAMBER SOCKET SYSTEM

(75) Inventor: Egill Sveinbjorn Egilsson, Reykjavik (IS)

(73) Assignee: Össur hf, Reykjavik (IS)

( * ) Notice: Subject to any disclaimer, the term of this patent is extended or adjusted under 35 U.S.C. 154(b) by 237 days.

(21) Appl. No.: 11/905,521

(22) Filed: Oct. 2, 2007

(65) Prior Publication Data

US 2008/0086218 A1 Apr. 10, 2008

Related U.S. Application Data

(60) Provisional application No. 60/850,337, filed on Oct. 10, 2006.

(51) Int. Cl.
*A61F 2/80* (2006.01)
(52) U.S. Cl. ......................................... 623/34
(58) Field of Classification Search .............. 623/27–38
See application file for complete search history.

(56) References Cited

U.S. PATENT DOCUMENTS

| 4,908,037 | A  | * | 3/1990 | Ross ............................. 623/32 |
| 6,287,345 | B1 | * | 9/2001 | Slemker et al. ................ 623/34 |
| 7,169,189 | B2 | * | 1/2007 | Bjarnason et al. ............. 623/37 |

* cited by examiner

*Primary Examiner*—Bruce E Snow
(74) *Attorney, Agent, or Firm*—Bacon & Thomas, PLLC

(57) ABSTRACT

A vacuum chamber socket system having a shell which defines a receiving portion for receiving a residuum. The receiving portion is connected via a vacuum transfer port to a vacuum reservoir chamber. A one-way or non-return valve is provided within the vacuum transfer port for allowing air to pass from the receiving portion into the chamber, but not from the chamber to the receiving portion. The chamber also includes an evacuation port for creating a partial vacuum within both the chamber and the receiving portion. A removable evacuation device may be connected to the evacuation port in order to create the partial vacuum.

18 Claims, 1 Drawing Sheet

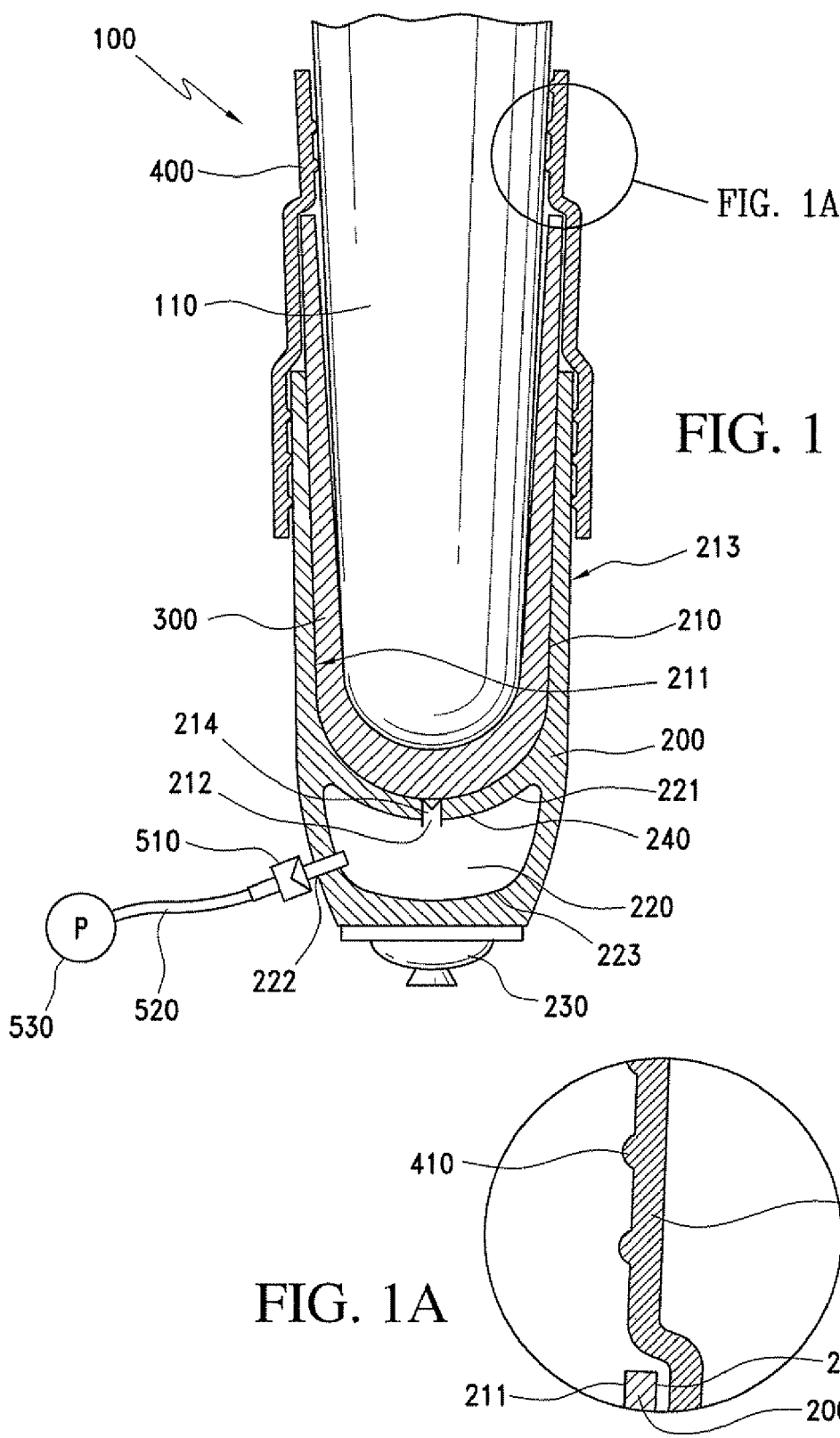

VACUUM CHAMBER SOCKET SYSTEM

CROSS-REFERENCE TO RELATED APPLICATIONS

This application claims the benefit of priority of U.S. Provisional Application No. 60/850,337, filed on Oct. 10, 2006.

FIELD OF THE INVENTION

The present invention relates generally to the field of prosthetic devices, and more particularly to a vacuum chamber socket system for use in retaining a prosthetic appliance on a residual limb.

BACKGROUND

Amputees have retained prosthetic devices on their residual limbs using various vacuum or suction arrangements for many years, particularly since the advent of soft cushion liners that are worn between the residual limb and the prosthetic socket. Typically, a one-way valve is provided at a distal end of an otherwise closed socket that is arranged to receive the distal end portion of a residual limb whereby air in front of the distal end of the residual limb may be exhausted through the one-way valve until the residual limb and a corresponding liner are fully inserted into the socket.

The one-way valve thereafter is maintained in a closed condition and forces tending to separate the prosthetic socket from the residual limb are resisted by induced sub-atmospheric pressure between the distal end of the residual limb and the distal end of the socket.

It is necessary, of course, with vacuum suspensions to maintain the sub-atmospheric pressure or vacuum at the distal end of the socket. Thus, appropriate sealing sleeves and other arrangements are typically provided to prevent influx of air around the distal end of the residual limb and into the distal end of the socket. Obviously, with a vacuum suspension system, any significant loss of vacuum will result in separation of the prosthetic socket from the residual limb unless an additional element is provided to retain the socket attached to the residual limb.

It has been recognized in the prior art to provide a vacuum reservoir chamber maintained at sub-atmospheric pressure and in communication with a prosthetic socket for the purpose of maintaining an appropriate partial vacuum within the socket in order to compensate for variations in volume of the residual limb while the prosthetic socket is worn and to compensate for air leakage around the residual limb. An integral system having vacuum pressure sensors and evacuation means is carried by the prosthetic socket, or by an extension of the prosthetic socket.

U.S. published patent application No. 2004/0260403-A1, published on Dec. 23, 2004, herein incorporated by reference and co-owned by the assignee of this disclosure, provides a self-contained vacuum chamber socket system without the additional system to maintain the vacuum within the chamber. This configuration is an improvement over a vacuum chamber socket system that includes the additional weight of vacuum pressure sensors and evacuation means. However, the unavoidable leakage of air into the socket can raise the pressure within the vacuum chamber. Once the pressure within the vacuum chamber rises to atmospheric pressure, the residuum may slide within the socket. This is due to the expandability and compressibility of the air that is within the vacuum chamber.

Thus, while it is known to use suction to maintain a residual limb within a socket, it is desirous to provide a suitable arrangement that does not require an integral system of pressure sensors and an evacuation means for maintaining a sub-atmospheric pressure between the residual limb and the inner walls of a socket despite variations in volume of the residual limb and further despite minor air leakage around the residual limb tending to relieve the vacuum within the socket.

SUMMARY

In order to provide an improved mechanism for retaining a prosthetic socket on a residuum, a vacuum chamber socket system according to the present disclosure is provided. Embodiments of a vacuum chamber socket system include a rigid, structural, load-bearing, air impervious shell or socket that defines a residuum receiving portion for receiving a residuum in a proximal portion thereof. The shell further defines a chamber, or a vacuum reservoir chamber that may be distally located and that shares a distal common wall with the receiving portion. The common wall includes at least one aperture, or vacuum transfer port having a one-way or non-return valve disposed therein which allows the receiving portion to communicate with the chamber. In this manner, when a residuum is received within the receiving portion, the air within the receiving portion is expelled from the receiving portion, through the one-way valve, and into the chamber.

The one-way or non-return valve disposed in each aperture allows communication between the chamber and the receiving portion to be a one-way communication, such that air may only pass from the receiving portion into the chamber, and air cannot pass from the chamber into the receiving portion. This feature prevents the movement of the residuum within the socket that occurs once the pressure within the chamber rises to atmospheric pressure.

In order to establish a partial vacuum in the chamber and the receiving portion when a residuum is contained therein, the chamber includes a port so that the inner volume of the chamber may be communicated to the atmosphere outside the shell. The port may have a one-way valve such that the air in the volume of the chamber can be evacuated from the chamber, but cannot renter the chamber, thus creating a partial vacuum within the chamber. A partial vacuum is also created within the receiving portion through the at least one aperture. The port may also have a release element to allow air to flow into the chamber in order to remove the partial vacuum within the chamber.

In order to create the partial vacuum within the chamber and the receiving portion, an evacuation device, such as an electric or manual pump, may be removably connected to the port for evacuating air from the receiving portion and the chamber.

The vacuum chamber socket system may include the use of a sealing sleeve that is disposed in sealing contact with an outer surface of the shell. The sealing sleeve is also disposed in sealing contact with the residuum, or in sealing contact with a prosthetic liner, in order to maintain the partial vacuum within the chamber and the receiving portion. The sealing sleeve may include annular protrusions at both a proximal and a distal portion of an inner surface of the sleeve in order to provide for improved sealing between the sleeve and the shell and the residuum or liner.

The chamber may be sealed, with the exception of the at least one aperture and the port. In alternative embodiments the chamber may be entirely located in the distal portion of the shell, or the chamber may have portions disposed circumferentially around the receiving portion.

In further embodiments, the shell can include a prosthetic adapter for connecting the socket to a utilitarian and/or an aesthetic prosthetic limb.

The numerous advantages, features and function of the vacuum chamber socket system will become readily apparent and better understood in view of the following description, appended claims, and accompanying drawings. The following description is not intended to limit the scope of the vacuum chamber socket system, but instead merely provides exemplary embodiments for ease of understanding.

BRIEF DESCRIPTION OF THE DRAWINGS

FIG. 1 is a cross-sectional view of an embodiment of a vacuum chamber socket system.

FIG. 1A is an enlarged inset view of a proximal portion of a sealing sleeve used in the vacuum chamber socket system shown in FIG. 1.

DETAILED DESCRIPTION OF VARIOUS EMBODIMENTS

A. Environment and Context of the Various Embodiments

The vacuum chamber socket system is described in view of a unitary socket shell construction for ease of illustration. Of course, any suitable configuration of the socket shell may be used. Exemplary configurations, materials and constructions for the socket shell are described in U.S. published patent application No. 2004/0260403-A1. One feature is that the shell and the receiving portion and chamber formed by the shell are structurally rigid and air impervious.

Embodiments of the vacuum chamber socket system may be incorporated into any number of prosthetic appliances. Some examples include above and below knee lower limb prosthetics, as well as upper limb prosthetics. While the advantages of the vacuum chamber socket system are discussed in detail with respect to lower limb prostheses, similar advantages are achieved when the vacuum chamber socket system is applied to upper limb prosthetics.

In order to better understand the operation and benefits of the vacuum chamber socket system described herein in relation to an above-knee or a below-knee prosthetic lower limb, a basic discussion of the gait cycle is required. The gait cycle defines the movement of the leg between successive heel contacts of the same foot. The gait cycle has two main phases, stance and swing, that can be broken down further into eight sub-phases. The stance phase has five time periods: heel-strike, or initial contact; loading response; mid-stance; terminal stance; and pre-swing. The swing phase has four time periods, one of which is shared with the stance phase. They are pre-swing, initial swing, mid swing and terminal swing.

The cyclic, repetitive motions of the stance phase and the swing phase create a pumping or pistoning effect within a prosthetic socket. This pistoning or pumping will tend to draw air into the socket during at least a portion of the pistoning or pumping. Even socket systems using some kind of a sealing system will allow some air to leak into the receiving portion of the socket.

The use of a vacuum reservoir chamber provides relief for the air that leaks into the socket during use, and thus maintains the seal between the residuum and the socket. Unfortunately, without a system of sensors and an automatic evacuation means, the pressure within the vacuum reservoir chamber will eventually reach atmospheric pressure. When this occurs, the volume of air in the vacuum reservoir chamber will act as an "air pocket," and will allow the residuum to move within the receiving portion of the socket shell.

For example, when the pressure within the vacuum reservoir chamber is at atmospheric pressure, the weight of the socket and lower limb prosthetic will cause the socket and the residuum to move relative to each other during any phase of the gait cycle where the weight of the lower limb prosthetic is not supported on the ground. This occurs because the pocket of air within the vacuum reservoir chamber is able to expand when it is at atmospheric pressure. This results in the socket and lower limb prosthetic sliding along the residuum under gravity or inertial loading, and thus expanding the air within the vacuum reservoir chamber until there is equalization between the pressures in the vacuum reservoir chamber and the receiving portion.

In a similar fashion, during mid-stance, when the entire weight of the user's body is transferred from the residuum through the socket to the lower limb prosthetic, the air at atmospheric pressure within the vacuum reservoir chamber is compressed until there is equalization between the pressures in the vacuum reservoir chamber and the receiving portion. This compression of the air within the vacuum reservoir chamber allows the residuum to move towards the distal end of the socket within the receiving portion.

Numerous problems can occur from this movement of the socket and the residuum relative to each other. For example, if a protective liner is not being used there can be chafing of the skin on the residuum. Even if a protective liner is used, the cyclic changes in pressure that are experienced by the distal portion of the residuum can cause other medical problems. In addition, the simple fact that there is movement between the socket and the residuum provides a user with insecurity regarding whether the socket will remain on the residuum.

By providing a one-way valve within the vacuum transfer port between the receiving portion of the shell and the vacuum reservoir chamber, the problems discussed above are alleviated or eliminated. During mid-stance, the distal portion of the residuum within the receiving portion of the socket shell temporarily increases the pressure in the distal portion of the receiving portion of the socket shell, due to the one-way valve positioned in the vacuum transfer port, which is normally closed.

When the pressure within the distal portion of the receiving portion is sufficient to overcome the threshold opening pressure of the one-way valve, the air that has leaked into the receiving portion of the socket will be forced into the vacuum chamber reservoir. Thus, when the valve closes, the partial vacuum within the receiving portion of the socket shell will be maintained, even when the pressure within the vacuum chamber is at atmospheric pressure or higher.

With the use of embodiments of the vacuum chamber socket system, there is little to no movement of the residuum within the receiving portion. The one-way valve isolates the vacuum reservoir chamber from the receiving portion. Thus, there is no large pocket of compressible air between the distal portion of the residuum and the one-way valve. Because there is no large pocket of compressible air, movement between the residuum and the socket is limited or completely eliminated.

Likewise, during any phase of the gait cycle where the socket and lower limb are not supported by the ground, movement between the residuum and socket is eliminated or limited. This is again due to the fact that there is no large pocket of air between the one-way valve and the residuum, since the one-way valve isolates the vacuum reservoir chamber from the receiving portion.

Thus, embodiments of the vacuum chamber socket system maintain a partial vacuum within the receiving portion, even when the pressure within the chamber has risen to atmospheric pressure, due to the fact that the one-way or non-return valve prevents the transfer of the higher pressure in the chamber to the receiving portion.

Thus, the residuum and socket of these embodiments behave like a vacuum retention socket system as long as the pressure within the chamber is less than atmospheric pressure. Then, once the pressure within the chamber equalizes to atmospheric pressure, the residuum and socket of this disclosure behave in the same manner as a conventional socket system. In this way, the partial vacuum within the receiving portion is maintained for longer periods of time, and once the pressure in the chamber equals atmospheric pressure, the residuum is maintained within the receiving portion in a conventional manner.

Another advantage of the chamber of this system is provided by the constant volume chamber defined by the rigid, structural, load-bearing, air impervious shell. The volume capacity of the chamber does not vary in the normal use of the socket, even under the cyclical loading typically encountered during the use of such sockets, for example in prosthetic legs during walking.

A constant volume chamber is advantageous since a variable volume chamber would cause insecurity to a user as to whether a proper vacuum is being maintained. The variable volume chamber allows movement of the socket that causes a user to be concerned as to whether the residuum is becoming loose from the socket.

It is important to note that the size of the volume of the chamber is one factor in determining how long the partial vacuum in the chamber and the receiving portion is maintained. For example, a larger chamber volume will maintain the partial vacuum within the chamber and the receiving portion for a longer period of time than a chamber having a lesser volume.

For further ease of understanding the vacuum chamber socket system as disclosed herein, a description of a few terms is necessary. As used herein, the term "proximal" has its ordinary meaning and refers to a location that is closer to the heart than another location. Likewise, the term "distal" has its ordinary meaning and refers to a location that is further from the heart than another location. Further, the terms "axial," "axially," "circumferential," and "circumferentially" all have their ordinary meaning and refer to locations along an axis and along a circumference, respectively.

B. Detailed Description of Embodiments

An embodiment of a vacuum chamber socket system 100 is shown in FIG. 1. A socket 200 for receiving a residuum 110 through the proximal portion of the socket 200 is shown. The socket 200 can be constructed of any suitable materials providing structural rigidity and support and imperviousness to air. Since the socket 200 is structurally rigid, it provides the user with the security that the socket will perform as expected under normal usage conditions. Specifically, the user will not have to be concerned that the volume of the socket 200 will change under load, which would otherwise affect the interface between the residuum 110 and the socket 200.

Since the socket 200 is also air impervious, a partial vacuum can be created between the residuum 110 and the socket 200 for maintaining the socket 200 on the residuum 110. The materials that the socket 200 is constructed from can themselves be air impervious or they can be provided with a coating that is air impervious, in a manner that is well known to skilled artisans. Exemplary materials for constructing the socket 200 include carbon or glass fiber resin composites and appropriate plastics.

The socket 200 may have a socket adapter 230 located at a distal portion of the socket shell 200 for connecting the socket to a prosthetic limb (not shown) such as a prosthetic knee, ankle, or elbow joint. The adapter 230 may be any suitable conventional adapter, such as a pyramid connection or a threaded connection. Some examples of conventional connections are part numbers A-135100, A-235300, A-335100, and A-435120 all available from Össur hf., Reykjavik, Iceland.

An embodiment of the socket 200 is shown in FIG. 1 having a unitary construction for forming a shell. The socket shell defines a receiving portion 210 for receiving a residuum 110, and a chamber 220 located in a distal portion of the socket shell. The receiving portion 210 may have a generally cylindrical or conical shape. In alternative embodiments, the receiving portion 210 may have a customized fit that closely corresponds to the shape of the residuum of a particular user.

Generally, the socket includes a rigid, structural, load-bearing, air impervious inner wall 211 in the form of a close ended cup having an open inner wall proximal end and a closed inner wall 213 distal end area. The inner wall defines an inner volume or the receiving portion, and is adapted to contain a distal portion of a residuum. The inner wall proximal end is adapted to receive a distal portion of a residuum to be located within the inner volume. The socket also includes a generally continuous, rigid, air impervious structural, load-bearing outer wall section having an outer wall section proximal end and a closed outer wall section distal end area.

In the illustrated embodiment, the chamber 220 has a unitary construction with the socket shell 200 and the receiving portion 210. The chamber 220 may have a cup shape wherein the circumferential wall portions of the chamber 220 are defined by extensions of the wall portions that define the receiving portion 210. The distal portion of the cup shaped chamber 220 shown in FIG. 1 may have suitable fasteners to retain the socket adapter 230. As a variation, the socket adapter 230 may be integrated into the distal portion of the cup shaped chamber 220 in a known manner, such as by use of adhesives or by fixing the socket adapter 230 within the same resin matrix that forms the socket shell 200.

As can be seen in the embodiment illustrated in FIG. 1, the cup shaped chamber 220 is enclosed at the proximal portion of the chamber 220 by a common wall 240 between the receiving portion 210 and the chamber 220. In this embodiment, the common wall 240 is also formed integrally with both the receiving portion 210 and the chamber 220. The chamber 220 can be considered to be defined, by way of the common wall 240, by an outer side 221 of the inner wall 211 and an inner side 223 of the outer wall section 213.

In variations, the chamber 220 may have any suitable configuration, such as a single chamber that is formed circumferentially around the receiving portion 210. Alternatively, multiple chambers 220 which extend axially along the receiving portion 210 and that are circumferentially spaced around the receiving portion 210 may be provided. A still further variation could include the distally located cup shaped chamber 220 in combination with these alternate configurations for the chamber.

While the socket shell 200, the receiving portion 210, and the chamber 220 are shown in a unitary construction, the socket shell can also be provided by components which form the receiving portion and the chamber separately, as exemplified in U.S. published patent application No. 2004/0260403-A1.

The provision of the chamber 220 allows a vacuum within the receiving portion 210 to be maintained, even when some air has managed to enter into the receiving portion 210. Any excess air that enters into the receiving portion 210 will tend to increase the pressure within the receiving portion 210, and thus reduce the effectiveness of the partial vacuum seal between the residuum 110 and the socket 200. The presence of the vacuum chamber 220 provides a reservoir for the excess air, so that the partial vacuum between the receiving portion 210 and the residuum 110 will be maintained. Vacuum chambers having different sizes of volumes can be provided in alternative embodiments in order to adjust how long the partial vacuum may be maintained.

At least one aperture or vacuum transfer port 212 is formed between the receiving portion 210 and the chamber 220. As shown in FIG. 1, one aperture 212 is shown in a distal portion of the receiving portion 210 connecting the receiving portion 210 to the chamber 220 so that a communication is established between the receiving portion 210 and the chamber 220. In this manner, a partial vacuum created in the chamber 220 may be communicated to the receiving portion 210, thus allowing the partial vacuum within the receiving portion 210 to be maintained, even though excess air may have entered the receiving portion 210.

Although only one aperture 212 is shown in the distal portion of the receiving portion 210 in FIG. 1, a skilled artisan will recognize that any suitable number of apertures may be located in any suitable manner within the receiving portion 210. For example, if a chamber 220 is provided circumferentially around the receiving portion 210, a plurality of apertures 212 may be provided axially and circumferentially spaced along the receiving portion 210. Further, as shown in FIG. 1, the aperture 212 is substantially smaller in cross-section than a closed inner wall distal end area of the shell 200.

A one-way or non-return valve 214, such as a check valve, is disposed within each aperture or vacuum transfer port 212. The one-way valve 214 allows air to flow from the receiving portion 210 into the chamber 220, but not in the other direction from the chamber 220 to the receiving portion 210.

As discussed above, the inclusion of the one-way or non-return valve 214 provides numerous benefits and advantages. The one-way or non-return valve 214 can have any suitable construction known to skilled artisans, and may take the form of duck-billed valves, slit valves, spring biased element check valves, such as ball check valves, resilient element check valves, or any other suitable one-way valve. The one-way or non-return valves can also be selected for use based upon their threshold actuation pressure, as will be recognized by the skilled artisan.

In order to provide a partial vacuum within the chamber 220 and the receiving portion 210, an aperture (222) formed along the side walls of the shell or an evacuation port 510 may be provided in the chamber 220 so that the internal volume of the chamber 220 may be in communication with the atmosphere external to the socket shell 200. A one-way or non-return valve may be provided separately or integrally with the evacuation port, as well as a release mechanism or element, as is well known in the art, for releasing the vacuum with in the chamber 220.

In an alternative embodiment, a vacuum chamber prosthetic socket system may be implemented and may include a vacuum connection 520, such as a tube or hose, that is removably connected to the evacuation port 510 at one end and is connected to an evacuation device, such as a manual or electric pump 530, at the other end so that the air within the chamber 220 may be evacuated to create a partial vacuum within the chamber 220 and the receiving portion 210 in order to retain the residuum 110 within the socket.

In this manner, the user of the vacuum chamber socket system can create a partial vacuum within the chamber 220 and the receiving portion 210 without having to transport the excess weight of an integral evacuation device, pressure sensors, computers, and manifolds or conduits. This reduction in weight reduces the energy required by the user to swing the prosthetic limb during the gait cycle.

Any suitable evacuation device recognized by a skilled artisan may be used, for example a manual or electric piston pump. Further, any suitable connection mechanisms recognized by a skilled artisan, such as hoses, tubes and fittings, may be provided.

In further embodiments of the vacuum chamber socket system, a user may use a prosthetic socket liner 300 in order to provide a partial vacuum along the entire interface between the receiving portion 210 and the residuum 110. Examples of suitable liners that allow the partial vacuum to be maintained along the entire interface are disclosed in U.S. published patent application No. 2004/0260403-A1.

Still further embodiments of the vacuum chamber socket system may use a sealing sleeve 400 in order to reduce the amount of air that may leak into the receiving portion 210. The sleeve 400 may include protrusions 410, as shown in FIG. 1A, arranged on an inner surface of the sleeve 400 in both the proximal and distal portions of the sleeve 400. The protrusions 410 provide for improved sealing between the sleeve 400 and the socket shell 200 and the residuum 110 or the liner 300. The sleeve 400 may be constructed from any suitable air impervious material, such as a non-porous, continuously cured elastomer such as silicone. Exemplary sleeves are disclosed U.S. published patent application nos. U.S. 2005/0267599-A1, and U.S. 2005/0267598-A1, both published on Dec. 1, 2005, which are incorporated by reference and co-owned by the assignee of this disclosure.

As an alternative, a suspension liner having a seal may be utilized in place of the liners discussed above. Exemplary liners are disclosed in co-pending U.S. patent application Ser. No. 11/516,500, filed Sep. 7, 2006, herein incorporated by reference and co-owned by the assignee of this disclosure. The use of a suspension liner having a seal near the distal end of the liner provides a much smaller volume between the liner and the shell where the partial vacuum must be maintained. Thus, a partial vacuum between the liner and the shell can be maintained for longer periods of time as compared to liners without the seal, assuming a vacuum chamber reservoir having the same volume.

In using liners having a seal, according to U.S. patent application Ser. No. 11/516,500, in the vacuum chamber socket system the sealing sleeve 400 described above may also be provided to further maintain the partial vacuum between the liner and the shell.

As discussed above, any socket system incorporating a vacuum or a partial vacuum in order to retain the socket on a residuum is subject to air leaks and a gradual increase in the pressure of the vacuum or partial vacuum. This is true even when a sealing system is provided.

In a socket system incorporating a vacuum reservoir chamber without means to maintain the vacuum, the air leakage will eventually allow the residuum to move within the receiving portion of the socket shell.

By providing one-way or non-return valves between the receiving portion and the vacuum reservoir chamber, the problem of the residuum moving within the receiving portion of the socket shell is alleviated. Thus, the disclosed vacuum chamber socket system provides an improved system for retaining the socket shell on a residuum.

Alternate configurations and materials for constructing the disclosed vacuum chamber socket system will be apparent to the skilled artisan. These alternate configurations and materials are intended to be included within the scope of the appended claims.

For example, further embodiments of a vacuum chamber socket system may include a plurality of chambers that each communicate with the receiving portion through at least one non-return or one-way valve. Each chamber would also have an evacuation port for creating a partial vacuum within the chambers and the receiving portion.

A still further embodiment could combine a single chamber within the distal portion of the shell and either a single chamber or a plurality of chambers spaced circumferentially around the receiving portion.

In embodiments employing a chamber or a plurality of chambers spaced circumferentially around the receiving portion and extending axially along the receiving portion, a plurality of vacuum transfer ports and one-way valves can be provided axially and circumferentially spaced around the common wall between each chamber and the receiving portion.

Of course, it is to be understood that not necessarily all objects or advantages may be achieved in accordance with any particular embodiment of the invention. Thus, for example, those skilled in the art will recognize that the invention may be embodied or carried out in a manner that achieves or optimizes one advantage or group of advantages as taught herein without necessarily achieving other objects or advantages as may be taught or suggested herein.

The skilled artisan will recognize the interchangeability of various features from different embodiments. In addition to the variations described herein, other known equivalents for each feature can be mixed and matched by one of ordinary skill in this art to construct a vacuum chamber socket system in accordance with principles of the present invention.

Although this invention has been disclosed in the context of certain exemplary embodiments and examples, it therefore will be understood by those skilled in the art that the present invention extends beyond the specifically disclosed embodiments to other alternative embodiments and/or uses of the invention and obvious modifications and equivalents thereof. Thus, it is intended that the scope of the present invention herein disclosed should not be limited by the particular disclosed embodiments described above, but should be determined only by a fair reading of the claims below.

The invention claimed is:

1. A prosthetic socket comprising: a rigid, structural, load-bearing, air impervious inner wall generally in the form of a close ended cup having an open inner wall proximal end and a closed inner wall distal end area, the inner wall defining an inner volume adapted to contain a distal portion of a residuum, and the inner wall proximal end adapted to receive a distal portion of a residuum to be located within the inner volume; a generally continuous, rigid, air impervious structural, load-bearing outer wall section having an outer wall section proximal end and a closed outer wall section distal end area; a chamber defined between an outer side of the inner wall and an inner side of the outer wall section; at least one aperture in the inner wall communicating the inner volume of the inner wall with the chamber, the aperture being substantially smaller in cross-section than the closed inner wall distal end area; a one-way valve disposed within the at least one aperture and the inner volume being in one-way communication with the chamber; and a port communicating the chamber to the atmosphere outside the outer wall section for establishing a partial vacuum within both the chamber and the inner volume in order to effect a vacuum suspension of the prosthetic socket on a residuum,
wherein the port comprises a one-way valve for allowing air to flow only from the chamber to the atmosphere outside the prosthetic socket.

2. The prosthetic socket according to claim 1, wherein the port further comprises a release element for allowing air to flow from the atmosphere outside the prosthetic socket into the chamber.

3. The prosthetic socket according to claim 1, further comprising a prosthetic adapter located along a base portion of the outer wall section distal end area.

4. The prosthetic socket according to claim 1, wherein the chamber is sealed other than the at least one aperture communicating with the receiving portion and the port.

5. A prosthetic socket comprising: a rigid, structural, load-bearing, air impervious inner wall generally in the form of a close ended cup having an open inner wall proximal end and a closed inner wall distal end area, the inner wall defining an inner volume adapted to contain a distal portion of a residual limb, and the inner wall proximal end adapted to receive a distal portion of a residual limb to be located within the inner volume; a generally continuous, rigid, air impervious structural, load-bearing outer wall section having an outer wall section proximal end and a closed outer wall section distal end area; a chamber defined between an outer side of the inner wall and an inner side of the outer wall section, the outer wall section distal end area having side walls forming part of the chamber; at least one aperture in the inner wall communicating the inner volume of the inner wall with the chamber; a one-way valve disposed within the at least one aperture and the inner volume being in one-way communication with the chamber; and a port formed through the thickness of the side walls of the outer wall section distal end area and communicating the chamber with an area external of the outer wall section, the port communicating to an area outside the outer wall section via a one-way check valve operational so as to selectively permit evacuation of air out of the chamber but not ingress of air into the chamber, the port defined by and extending through a thickness of the outer wall section.

6. The prosthetic socket according to claim 5, wherein the port further comprises a release element for allowing air to flow from the atmosphere outside the prosthetic socket into the chamber.

7. The prosthetic socket according to claim 5, further comprising a prosthetic adapter located along a base portion of the closed outer wall section distal end area.

8. The prosthetic socket according to claim 5, wherein the chamber is sealed other than the at least one aperture communicating with the receiving portion and the port.

9. A prosthetic socket system comprising:
a rigid, air impervious socket defining a receiving portion for receiving a residuum in a proximal portion thereof, and a distally located chamber sharing a common wall with the receiving portion, the common wall including at least one aperture extending therethrough located at a distal end section of the socket;
a one-way valve disposed within the at least one aperture such that the receiving portion is in one-way communication with the chamber so that air within the receiving portion may be expelled through the one-way valve and into the chamber when a residuum is received within the receiving portion;
a port communicating the chamber to the atmosphere outside the socket for establishing a partial vacuum within both the chamber and the receiving portion in order to effect a vacuum suspension of the socket on a residuum;

a sealing sleeve disposed in sealing contact with an outer surface of the proximal portion of the socket and for being disposed in sealing contact with a residuum, so that the partial vacuum in the chamber and the receiving portion is maintained; and wherein the port comprises a one-way valve for allowing air to flow only from the chamber to the atmosphere outside the shell.

10. The prosthetic socket system according to claim 9, wherein the port further comprises a release element for allowing air to flow from the atmosphere outside the shell into the chamber.

11. The prosthetic socket system according to claim 9, further comprising a prosthetic adapter located at a distal end area of the socket.

12. The prosthetic socket system according to claim 9, wherein the chamber is sealed other than the at least one aperture communicating with the receiving portion and the port.

13. The prosthetic socket system according to claim 9, wherein the sealing sleeve comprises a plurality of annular protrusions disposed on the inner surface of the sleeve in both a proximal and distal region of the sleeve.

14. The prosthetic socket system according to claim 9, further comprising a liner for being received on a residuum, such that when a residuum is placed within the receiving portion, the liner contacts an inner surface of the receiving portion.

15. The prosthetic socket system according to claim 14, further comprising a sealing sleeve disposed in sealing contact with an outer surface of the proximal portion of the shell and for being disposed in sealing contact with the liner, so that the partial vacuum in the chamber and the receiving portion is maintained.

16. The prosthetic socket system according to claim 15, wherein the sealing sleeve comprises a plurality of annular protrusions disposed on the inner surface of the sleeve in both a proximal and distal region of the sleeve.

17. The prosthetic socket system according to claim 9, further comprising an evacuation device removably connected to the port for creating the partial vacuum within the chamber and the receiving portion.

18. The prosthetic socket system according to claim 9, wherein the port is formed through a thickness of a distal end area side wall of the shell.

\* \* \* \* \*